(12) United States Patent
Telandro et al.

(10) Patent No.: US 6,383,219 B1
(45) Date of Patent: *May 7, 2002

(54) IMPLANT FOR DEEP SCLERECTOMY

(75) Inventors: Alain Telandro, Cannes; Philippe Sourdille, La Baule; Valérie Jallet, Meythet; Gilles Bos, La Balme de Sillingy; Franck Villain, Annecy, all of (FR)

(73) Assignee: Corneal Industrie, Pringly (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/367,421
(22) PCT Filed: Feb. 16, 1998
(86) PCT No.: PCT/FR98/00291
  § 371 Date: Aug. 12, 1999
  § 102(e) Date: Aug. 12, 1999
(87) PCT Pub. No.: WO96/40005
  PCT Pub. Date: Dec. 19, 1996

(30) Foreign Application Priority Data

Feb. 17, 1997 (FR) .............................. 97 01801

(51) Int. Cl.[7] .................................................. A61F 2/14
(52) U.S. Cl. ............................................ 623/4.1; 604/8
(58) Field of Search ................................ 623/4.1, 5.11, 623/5.16, 905, 906, 915, 924–926; 604/8

(56) References Cited

U.S. PATENT DOCUMENTS

| | | |
|---|---|---|
| 4,716,154 A | 12/1987 | Mälson et al. |
| 4,946,436 A | 8/1990 | Smith |
| 5,433,701 A | 7/1995 | Rubinstein |
| 5,558,630 A | 9/1996 | Fisher |
| 5,882,327 A * | 3/1999 | Jacob ............................ 604/8 |

FOREIGN PATENT DOCUMENTS

| | | |
|---|---|---|
| GB | 2 296 663 | 7/1996 |
| SU | 1066591 | 1/1984 |
| WO | WO 89/07426 | 8/1989 |
| WO | WO 94/13234 | 6/1994 |
| WO | WO 95/35078 | 12/1995 |
| WO | WO 96/40005 | 12/1996 |

* cited by examiner

Primary Examiner—David H. Willse
(74) Attorney, Agent, or Firm—Wolf, Greenfield & Sacks, P.C.

(57) ABSTRACT

The invention concerns an implant for deep sclerectomy for draining aqueous humor during surgical treatment of glaucoma. The implant is made of crosslinked hyaluronic acid and has substantially the shape of a polyhedron with at least five faces, advantageously the shape of a polyhedron with five or six faces. In a preferred embodiment, the implant has substantially the shape of a prism, advantageously straight with a trapezoidal base.

27 Claims, 1 Drawing Sheet

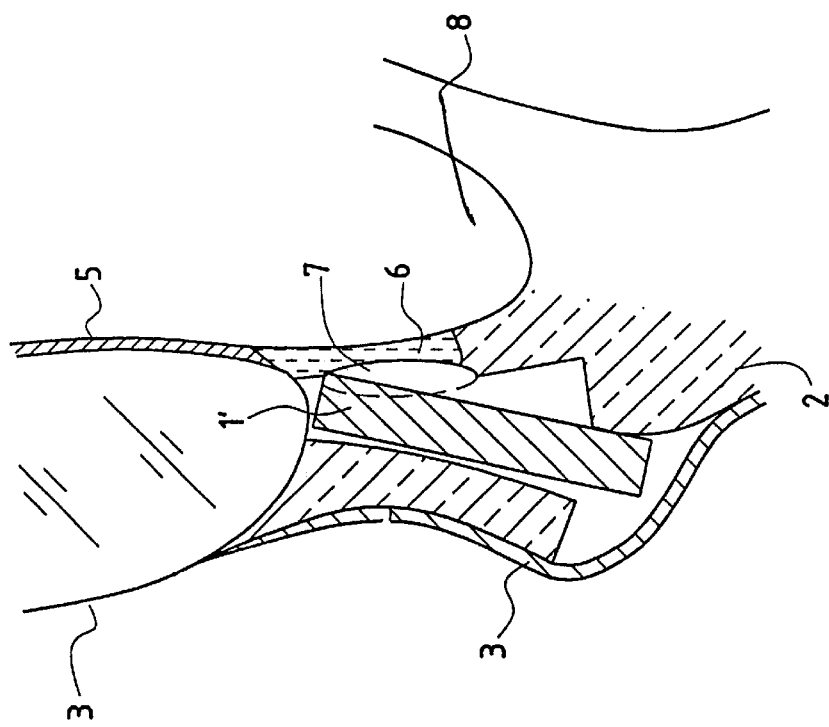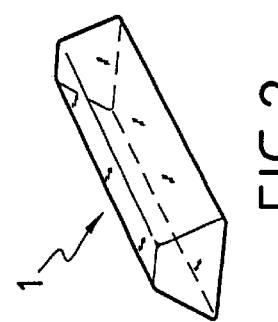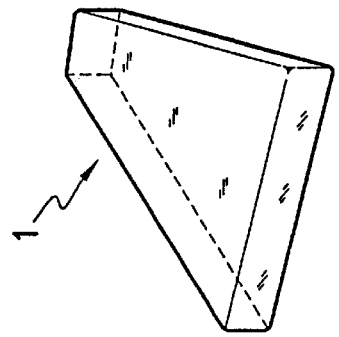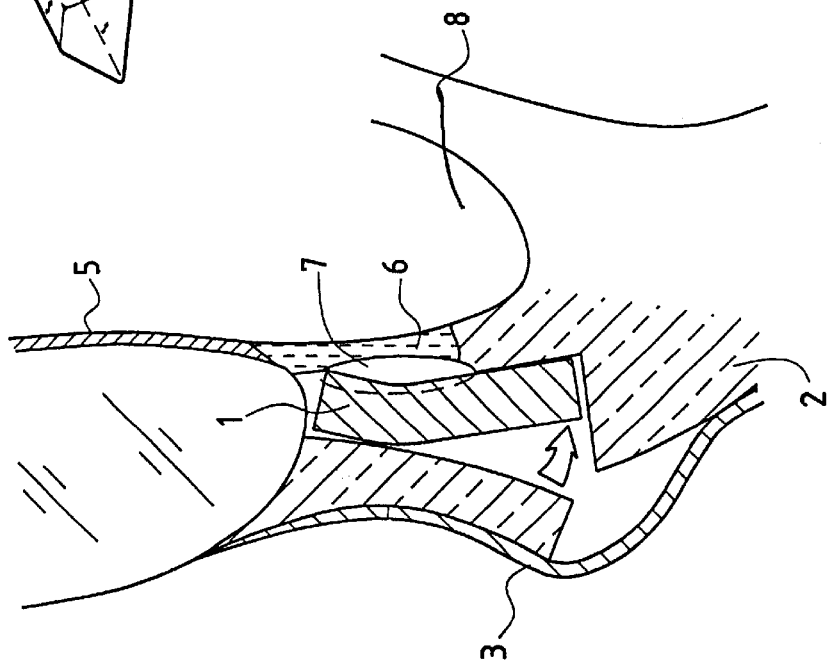

IMPLANT FOR DEEP SCLERECTOMY

The present invention relates to an implant for deep sclerectomy. Said implant of the invention is characterized by the material constituting it and by its shape.

The surgical technique of deep sclerectomy has been proposed recently for treating glaucoma. In effect, when the glaucoma connot be treated medically, it is necessary to intervene surgically to reduce the intraocular pressure.

The most current operatory technique is trabeculotomy. Said trabeculotomy consists in making an opening through the trabeculum, in order to evacuate the aqueous humor from the anterior chamber towards the subconjunctival space. A filtration bulla then generally appears beneath the conjunctiva 3, provoked by the accumulation of said aqueous humor beneath said conjunctiva. The complications associated with this surgical technique are fairly numerous. They consist in precocious or late hypotoniae, in reductions in depth of the anterior chamber and even in the collapse thereof, in a choroidal lift . . . One of the most dramatic complications is the secondary rupture of said filtration bulla, which may cause an endophthalmitis.

In order to avoid opening the anterior chamber 8, other surgical techniques have been proposed. One of these techniques, within the framework of which the present invention is included, is deep (so-called non-perforating) sclerectomy of the glaucoma. It consists in incising the sclera 2 until plumb with Schlemm's canal 7. The aqueous humor then gushes through the trabeculum 6. In order to assist the flow of said aqueous humor, it has been proposed to place, in said incision (in the deep scleral bed), a collagen implant, cylindrical in shape (the anterior end of said implant, opposite Schlemm's canal 7). Said implant facilitates said flow of said aqueous humor, performing the role of a wick (it transports the ocular fluids by capillarity). Results of implementation of this technique (deep sclerectomy associated with the placing of a collagen implant), of which the principle is recalled, are presented in Ophtalmologie 1995; 9: 666–670. A great future does not seem promised for said implant, due to its shape and the nature of the material consituting it. In effect, the cylindrical shape is not the shape most adapted to the anatomy of the eye and the material used—collagen of animal origin—is no longer recommended in view of the problems associated with the Creutzfeldt-Jakob syndrome.

BRIEF DESCRIPTION OF THE DRAWINGS

FIG. 1 is a partial cross-sectional side view illustrating placement of one embodiment of the invention in the sclera of the eye;

FIG. 1A is a partial cross-sectional side view illustrating placement of another embodiment of the invention in the sclera of the eye;

FIG. 2 is a perspective view illustrating one embodiment of the invention; and

FIG. 2A is a perspective view illustrating another embodiment of the invention.

The applicant is at present proposing an implant 1 which, within the framework of this surgical technique of (non-perforating) deep sclerectomy with implant, advantageously replaces said collagen implant, of cylindrical shape, of the prior art. Said implant of the invention as shown in FIGS. 1 and 1A—thanks to the characteristics of the material constituting it and to its geometrical shape—occupies for a longer period the space created surgically and efficiently allows the flow of the aqueous humor from the anterior chamber (without opening the latter); it constitutes a veritable drain.

Said implant 1 of the invention—implant for deep sclerectomy intended to drain the aqueous humor—is made of crosslinked hyaluronic acid and presents substantially the shape of a polyhedron with at least five faces. Advantageously, it presents substantially the shape of a polyhedron with five or six faces.

Such a polyhedral implant which therefore presents at least five species is relatively blocked once positioned in the space created; said implant further presenting, of course a volume adapted to the volume of said space. It should be possible to insert it in said space and then have it perform its function of wick, of veritable drain.

The person skilled in the art will understand the qualifying adverb "substantially" employed with reference to the shape of the implants of the invention perfectly well, in view of the nature of the material constitutint them. We shall return to said material hereinbelow in the present text.

Said implants of the invention advantageously present substantially the shape of a convex polyhedron, with at least five faces; said convex polyhedron having at least one substantially plane base (which constitutes its face or one of its faces of largest surface) which presents at least 3 sides and a small thickness. Thickness of said implants of the invention is understood to mean the maximum distance between said base and the apex opposite or the face opposite said base. Said thickness—small, generally included between 0.2 and 2 mm—is advantageously included between $\frac{1}{12}$th and $\frac{1}{4}$ (preferably between $\frac{1}{10}$th and $\frac{1}{8}$th of the length of the largest side of said base (with at least 3 sides).

Said (substantially plane) base, defined by a polygon with at least three sides, advantageously consists in a triangle or a quadrilateral, more particularly in a, trapezium (preferable isosceles) as shown in FIG. 2 and 2A.

Said "substantially" plane base (by the nature of the material constituting the implant) is, however, advantageously slightly incurved so that, once the implant is positioned, it follows the radius of curvature of the eye. According to this advantageous variant, its surface is therefore slightly concave.

Within the scope of advantageous variants of the invention, the implants present substantially:

the shape of an advantageously straight prism, with trapezoidal base (the trapezium of the base of such a prism is preferably an isosceles trapezium) or triangular; or the shape of a parallelepiped, advantageously a straight parallelepiped, and preferably a rectangular parallelepiped.

It is clear that, according to other variants, said polyhedral implants may present other shapes and in particular those of pyramids with rectangular or square base, those of such pyramids truncated, those of prisms, particularly straight ones, with any base . . .

It is recalled here that, generally, the base of the implant 1 of the invention (at least one of them; intended to be positioned along Descemet's membrane 5 and the internal wall of the sclera 2) is advantageously slightly incurved.

Furthermore, likewise generally, the angles of the polyhedron constituting the implant of the invention are advantageously blunt. This may constitute an advantage with reference to possible problems of traumatisms.

We shall now come to the nature of the material constituting the implants of the invention. It is question of crosslinked hyaluronic acid, sufficiently crosslinked to constitute a solid implant.

Hyaluronic acid is a glycosaminoglycan or mucopolysaccharide of high molecular weight which is found in animal tissues such as umbilical cords, the vitreous humor, the synovial liquid, condylomas, the skin, connective tissues (joints, tendons . . . ) . . . Said acid may thus be obtained naturally by extraction from certain of said animal tissues (in particular the condylomas and umbilical cords). It may also be obtained by bacterial fermentation. Said acid presents a high propensity for absorbing water. It is a very hydrophilic material whose water content, at equilibrium, is greater than 99%. Said material is perfectly suitable for ensuring the function of drain desired for the implant of the invention.

The chemical structure of said acid is that of a polymer presenting disaccharidic monomers of N-acetyl-D-glucosamine and of D-glucoronic acid, said amine and said acid being connected by a glucosidic β1→3 bond. The disaccharidic monomers are connected together by glucosidic β1→4 bonds in order to generate the non-crosslinked polysaccharidic chain without branching.

However, said chain presents, at the level of its monomers, functions, particularly hydroxyl ones, which allow it to be crosslinked chemically in order to create a more or less dense network.

In the present text and claims which accompany it, the term hyaluronic acid is employed as a generic name for designating both hyaluronic acid per se and its salts, particularly salts of hyaluronate. The implants of the invention are therefore based on a polymer selected from crosslinked hyaluronic acid and the crosslinked salts of said acid. Advantageously, they are based on crosslinked sodium hyaluronate. Said intervening sodium hyaluronate is advantageously of bacterial origin.

Said hyaluronic acid intervenes, within the framework of the invention, solid, crosslinked at a sufficient rate of crosslinking. It is recommended to carry out said crosslinking, via the hydroxyl functions of said acid, by means of a crosslinking agent presenting reactive functions; said agent intervening in quantities such that the ratio: total number of reactive functions of said crosslinking agent (intervening in the reactional medium)/total number of disaccharide repeating units of the molecules of hyaluronic acid (present in the reactional medium) is included between 0.2 and 1.

A minimum crosslinking assures the desired effect: the obtaining of a solid, presenting minimum mechanical resistance.

A maximum crosslinking is advantageously not exceeded. In effect, the intervention of a large quantity of crosslinking agent denatures the implants of the invention.

By way of crosslinking agent, there may be used, for making the implants of the invention, any agent known for crosslinking the hyaluronic acid via its hydroxyl functions—at least bifunctional crosslinking agent—and in particular a polyepoxide or its derivatives. By way of such a crosslinking agent, there may be used in particular epichlorhydrine, divinylsulfone, 1,4-bis(2,3-epoxypropoxy)butane (or 1,4-bis (glycidyloxy)butane or 1,4-butanediol diglycidyl ether= BDDE), 1,2-bis(2,3-epoxypropoxy)ethylene, 1-(2,3-epoxypropyl)-2,3-epoxy cyclohexane . . . Numerous crosslinking agents suitable for carrying out crosslinking of hyaluronic acid have been described in particular in U.S. Pat. No. 4,716,154.

It is not excluded from the scope of the invention to employ a plurality of crosslinking agents in order to obtain a crosslinked hyaluronic acid in which an implant of the invention is cut.

According to an advantageous variant, a crosslinking agent whose reactive functions are epoxy functions is used for preparing said crosslinked hyaluronic acid.

Generally, the carrying out of crosslinking of hyaluronic acid (or of one of its salts) is a familiar process for the person skilled in the art.

Originally, within the scope of the present invention, said crosslinked hyaluronic acid is used for producing polyhedral implants with at least five faces, suitable by way of implants for deep sclerectomy. Said implants are very hydrophilic due to the material constituting them and efficiently ensure evacuation of the aqueous humour from the anterior chamber.

The implants of the invention—polyhedrons with at least 5 faces, made of crosslinked hyaluronic acid—possibly have at least one active principle incorporated therein. Said active ingredient may in particular consist of an antibiotic and/or an antimitotic. There is no particular difficulty in incorporating active principle(s) in the mass of said implants of the invention. This is generally carried out during a step of hydration of said implants.

Finally, the implants of the invention are obtained by cutting out the adequate shape from a block of crosslinked hyaluronic acid. As said block generally presents a small thickness, we speak rathermore of lamella. The implants of the invention are positioned without particular difficulty through an adequate incision. Said incision was previously made to produce the space or cavity for implantation.

The present invention also covers an original application—by way of implant for deep sclerectomy, intended to drain the aqueous humour—of a substantially polyhedral mass with at least five faces (advantageously with five or six faces), made of crosslinked hyaluronic acid.

In fact, it also has for an object:

an original use of the crosslinked hyaluronic acid for the production of an implant for deep sclerectomy, presenting substantially the shape of a polyhedron with at least five faces, advantageously substantially the shape of a polyhedron with five or six faces; implant intended to drain the aqueous humour;

the carrying out of deep sclerectomy—non-perforating surgery of the glaucoma—with the intervention of an implant, in the above-mentioned material, of the above-mentioned shape.

In order to illustrate, in non-limiting manner, the invention presently claimed, an example of preparation of implants of the invention is attached to the above description.

The protocol followed is as follows:

1.00 g of sodium hyaluronate (with a molecular mass of $2.10^6$ Da) is dissolved in 7.80 g of an aqueous 0.25 M sodium hydroxide solution;

0.192 g of BDDE (crosslinking agent: 1,4-butanediol diglycidyl ether) are added to the solution;

after homogenization, the latter is placed in a water bath at 50° C. for 2 hours, a solid gel is then obtained which is hydrated up to equilibrium in deionized water;

said gel is then purified by continuous extraction, by de-ionized water, in a Soxhlet apparatus;

the gel thus purified is placed in equilibrium in a phosphate buffer solution at pH 7.2;

lamellae of 0.5 mm thickness are then cut out therefrom;

finally, these lamellae are bored into, with the aid of a bit presenting a trapezoidal cross-section (isosceles trapezium of which the bases measure respectively 3 and 0.5 mm and the height 5 mm); implants are then obtained which have substantially the shape of straight prisms with trapezoidal base and whose thickness varies between 0.5 and 1 mm.

What is claimed is:

1. An implant for deep sclerectomy, intended to drain the aqueous humor, made of crosslinked hyaluronic acid and presenting substantially the shape of a polyhedron with at least five faces wherein at least one face is structured to direct flow of the aqueous humor.

2. The implant of claim 1, wherein it presents substantially the shape of a polyhedron with five or six faces.

3. The implant of claim 1, wherein it presents substantially the shape of a convex polyhedron; said convex polyhedron having at least a substantially plane base which presents at least 3 sides and a small thickness; said thickness being defined as the maximum distance between said base and an apex opposite or a face opposite said base.

4. The implant of claim 3, wherein said thickness is included between $1/12$th and $1/4$ of the length of the largest side of said base.

5. The implant of claim 3, wherein said base has a triangular or trapezoidal shape.

6. The implant of claim 3, wherein said base is slightly incurved so that, once the implant is positioned, it follows a radius of curvature of the eye.

7. The implant of claim 1, wherein it presents substantially the shape of a prism with trapezoidal base.

8. The implant of claim 7, wherein it presents substantially the shape of a straight prism with trapezoidal base.

9. The implant of claim 1, wherein its apices are blunt.

10. The implant of claim 1, wherein said hyaluronic acid has been crosslinked, via its hydroxyl functions, by means of a crosslinking agent presenting reactive functions; said agent intervening in quantities such that the ratio: total number of reactive functions of said crosslinking agent/total number of disaccharidic repeating units of the molecules of hyaluronic acid, is included between 0.2 and 1.

11. The implant of claim 10, wherein said reactive functions of said crosslinking agent are epoxy functions.

12. The implant of claim 1, wherein said crosslinked hyaluronic acid has at least one active principle incorporated therein.

13. The implant of claim 1, wherein its thickness is about 2 mm.

14. A method for treating glaucoma according to the surgical technique of deep sclerectomy carried out with an implant, said method comprising incising the sclera until plumb with Schlemm's canal to generate a cavity in the deep scleral bed, inserting in said cavity an implant, wherein said implant is made of crosslinked hyaluronic acid and presents substantially the shape of a polyhedron with at least five faces.

15. The method of claim 14, wherein said implant presents substantially the shape of a polyhedron with five or six faces.

16. The method of claim 14, wherein said implant presents substantially the shape of a convex polyhedron; said convex polyhedron having at least a substantially plane base which presents at least 3 sides and small thickness; said thickness being defined as the maximum distance between said base and an apex opposite or a face opposite said base.

17. The method of claim 16, wherein said thickness is included between $1/12$th and $1/4$ of the length of the largest side of said base.

18. The method of claim 16, wherein said base has a triangular or trapezoidal shape.

19. The method of claim 16, wherein said base is slightly incurved so that, once the implant is positioned, it follows a radius of curvature of the eye.

20. The method of claim 14, wherein said implant presents substantially the shape of a prism with trapezoidal base.

21. The method of claim 20, wherein said implant presents substantially the shape of a straight prism with trapezoidal base.

22. The method of claim 14, wherein the apices of said implant are blunt.

23. The method of claim 14, wherein said hyaluronic acid has been crosslinked, via its hydroxyl functions, by means of a crosslinking agent presenting reactive functions; said agent intervening in quantities such that the ratio: total number of reactive functions of said crosslinking agent/total number of disaccharidic repeating units of the molecules of hyaluronic acid, is included between 0.2 and 1.

24. The method of claim 23, wherein said reactive functions of said crosslinking agent are epoxy functions.

25. The method of claim 14, wherein said crosslinked hyaluronic acid has at least one active principle incorporated therein.

26. A deep sclerectomy implant made of crosslinked hyaluronic acid having substantially the pre-formed shape of a polyhedron with at least five faces and a thickness of about 2 mm, wherein at least one face is structured to direct flow of the aqueous humor.

27. A method for reducing the intra-ocular pressure in the eye of a mammalian patient, comprising:

incising the sclera of an eye until plumb with Schlemm's canal to generate a cavity in the deep scleral bed, and inserting an implant in said cavity, wherein said implant is made of crosslinked hyaluronic acid having substantially the shape of a polyhedron with at least five faces, to allow increased aqueous humor outflow from the anterior chamber of the eye, and reduce the intraocular pressure.

* * * * *